United States Patent [19]
Bull et al.

[11] Patent Number: 4,689,224
[45] Date of Patent: * Aug. 25, 1987

[54] METHOD FOR ADMINISTERING VACCINES CONTAINING EQUINE LEUKOKINES AND COMPOSITIONS THEREFOR

[75] Inventors: Robert W. Bull, Haslett; Robert M. Soltysiak; Paul D. Minnick, both of East Lansing, all of Mich.

[73] Assignee: Neogen Corporation, Lansing, Mich.

[ * ] Notice: The portion of the term of this patent subsequent to Oct. 28, 2003 has been disclaimed.

[21] Appl. No.: 905,447

[22] Filed: Sep. 10, 1986

Related U.S. Application Data

[63] Continuation-in-part of Ser. No. 785,001, Oct. 7, 1985, Pat. No. 4,619,827.

[51] Int. Cl.$^4$ .................... A61K 39/12; A61K 45/02
[52] U.S. Cl. ........................... 424/89; 424/85; 424/86; 424/88
[58] Field of Search ............... 424/89, 85, 86, 88

[56] References Cited

U.S. PATENT DOCUMENTS

| | | | |
|---|---|---|---|
| 3,518,347 | 6/1970 | Pavilanis et al. | 424/89 |
| 3,699,222 | 10/1972 | Isaacs et al. | 424/85 |
| 3,790,665 | 2/1974 | Carlson et al. | 424/92 X |
| 3,793,150 | 2/1974 | Usdin | 424/92 X |
| 3,906,092 | 9/1975 | Hilleman et al. | 424/89 |
| 3,919,411 | 11/1975 | Glass et al. | 424/89 X |
| 3,970,749 | 7/1976 | Baugh | 424/85 X |
| 4,009,258 | 2/1977 | Kilbourne | 424/89 |
| 4,303,645 | 12/1981 | Carmichael et al. | 424/89 |
| 4,466,957 | 8/1984 | Hjorth et al. | 424/89 |
| 4,503,035 | 3/1985 | Pestka et al. | 424/85 |
| 4,619,827 | 10/1986 | Bull et al. | 424/89 |

OTHER PUBLICATIONS

Litvinov, Chem. Abstracts, 67, 7536, 80070u, 1967.
Antibiotiki, 12(7), 602–604 (1967), Litvinov.
Iscove et al., J. Exp. Med. 147, 923–933 (1978).
Langford et al., Methods in Enzymology, 78, p. 339, (1981).
Hierholzer, Appl. Microbiol. 18, 824–833 (1969).

*Primary Examiner*—Howard E. Schain
*Attorney, Agent, or Firm*—Ian C. McLeod

[57] ABSTRACT

A method for enhancing a vaccine immune response in mammals, including mice, equines, canines and felines using leukokines, particularly mixed leukokines, is described. The leukokines can be administered separately or admixed with the vaccine. The method and vaccine compositions are particularly effective where equine influenza vaccine or canine parvovirus vaccine and mixed leukokines are administered together to the equine or canine.

17 Claims, 10 Drawing Figures

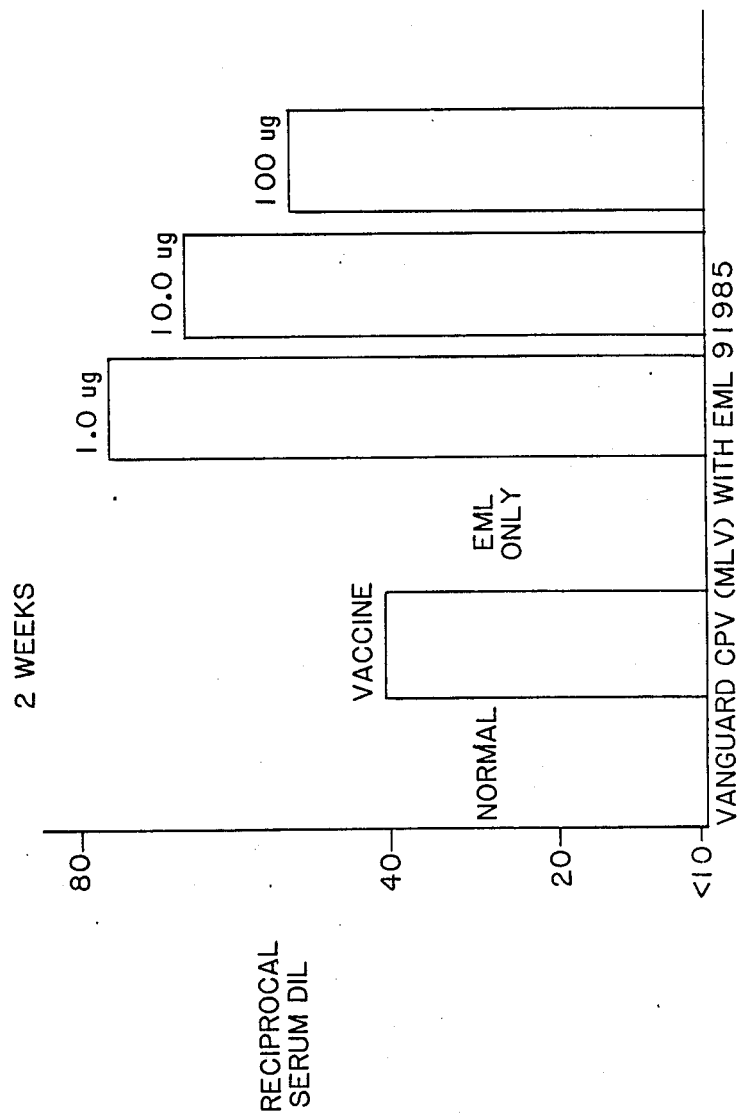

METHOD FOR ADMINISTERING VACCINES CONTAINING EQUINE LEUKOKINES AND COMPOSITIONS THEREFOR

CROSS-REFERENCE TO RELATED APPLICATION

This application is a continuation-in-part of U.S. application Ser. No. 785,001, filed Oct. 7, 1985, now U.S. Pat. No. 4,619,827.

BACKGROUND OF THE INVENTION (1) Field of the Invention

The present invention relates to a vaccination method for mammals wherein the vaccine is potentiated in its antibody response by a leukokine or mixed leukokines administered with the vaccine. In particular, the present invention relates to the potentiation of an equine influenza vaccine or a canine parvovirus vaccine or a murine administered vaccine with mixed equine leukokines.

(2) Prior Art

The term "interferon" is generally used by the prior art to refer to induced proteins of leucocyte and of fibroblast origins which interfere with viral replication. The terms "leukokine" or "leucokine" have been used in the recent literature to characterize proteins including interferons of leukocyte origins and the term leukokine is used herein.

The prior art relating to interferon is extensive. U.S. Pat. No. 3,699,222 (1972) to Isaacs and Lindenmann describes the original research with interferon as an antiviral agent. U.S. Pat. No. 4,503,035 (1985) to Pestka and Rubinstein describes purified interferons and in particular the use of leukocytes and a virus (Newcastle Disease virus) for inducing the interferons. Example 7 of this patent particularly describes the use of this procedure to produce equine interferon.

The presence of interferons in the blood stream with virus vaccines is known. U.S. Pat. No. 3,906,092 to Hilleman, Tytell and Woodhour (1975) describes the use of inducing polynucleotides as adjuvants to non-replicating (killed virus) vaccines to enhance antibody formation. The polynucleotides can induce interferon although interferon does not appear to be responsible for the result achieved by Hilleman et al. An adjuvant is necessary to achieve the results disclosed. The administration of mixed live Newcastle disease virus vaccine and interferon to provide an enhanced protection for chickens is described as prior art in this patent, but there is no description of the administration of interferon and a non-replicating virus vaccine. There does not appear to be an enhanced antibody response.

Vaccination with commercially available inactivated equine influenza virus vaccine alone (consisting of killed virus of tissue culture origin) produces a variable humoral immune antibody response in equines. This variation is in the magnitude of the antibody response, the time course in which the equine responds to the vaccine, and the duration of the antibody response. These variations have been recognized and accepted as due to biological variation of the species' immune system. Where there is an urgent need for immunity, the equine is repeatedly vaccinated with influenza vaccine.

New and more potent vaccines which augment the equine's immune response to influenza or other viral vaccine vaccination and thereby greatly increase both the likelihood and extent of a protected period with less frequent vaccination, are needed. Further, vaccines are needed where there is a less variable response to the vaccination.

In canines there is a need for early vaccination to prevent diseases such as parvovirus, distemper, rabies and adenovirus. The problem is that the puppies have maternal antibodies to any vaccine, which prevents early vaccination. Other animals, particularly cats, have the same problem. It would be highly desirable if vaccines could be developed for effective early vaccination of young animals while the maternal antibodies are still present.

OBJECTS

It is therefore an object of the present invention to provide improved vaccine compositions containing an admixture of a replicating or non-replicating virus vaccine and of a leukokine as an adjuvant, wherein there is an enhanced antibody response to the vaccine from use of the composition in mammals. Further it is an object of the present invention to provide a method for administering the vaccine with the leukokine which provides the improved response. It is particularly an object of the present invention to provide an improved method and vaccine compositions for providing immunity to equine influenza. Further it is an object of the present invention to provide a method for early vaccination of mammals, particularly dogs and cats, even in the presence of maternal antibodies. These and other objects will become increasingly apparent by reference to the following description and the drawings.

IN THE DRAWINGS

FIG. 1 is a graph of serum antibody response in equines to separate and concurrent coadministered injections of bivalent equine influenza vaccine (Haver-Lockhart Labs, Shawnee, Kansas) combined Miami and Prague strains) (1) Equi-1 and Equi-2 with a level of equine leukokines of 1350 mouse immunopotentiating units (IPU) (200,000 Antiviral Units, (AVU)) or (2) with no leukokines. The equines had a high initial serum antibody titer of 1:60 or higher to A/Equi-2/Miami/1/63 which appears to indicate some level of immunity most likely as a result prior exposure to influenza virus.

FIGS. 8 to 10 are bar graphs showing antibody response as a function of the use of leukokine with various vaccines in mice.

GENERAL DESCRIPTION

Figure 1:
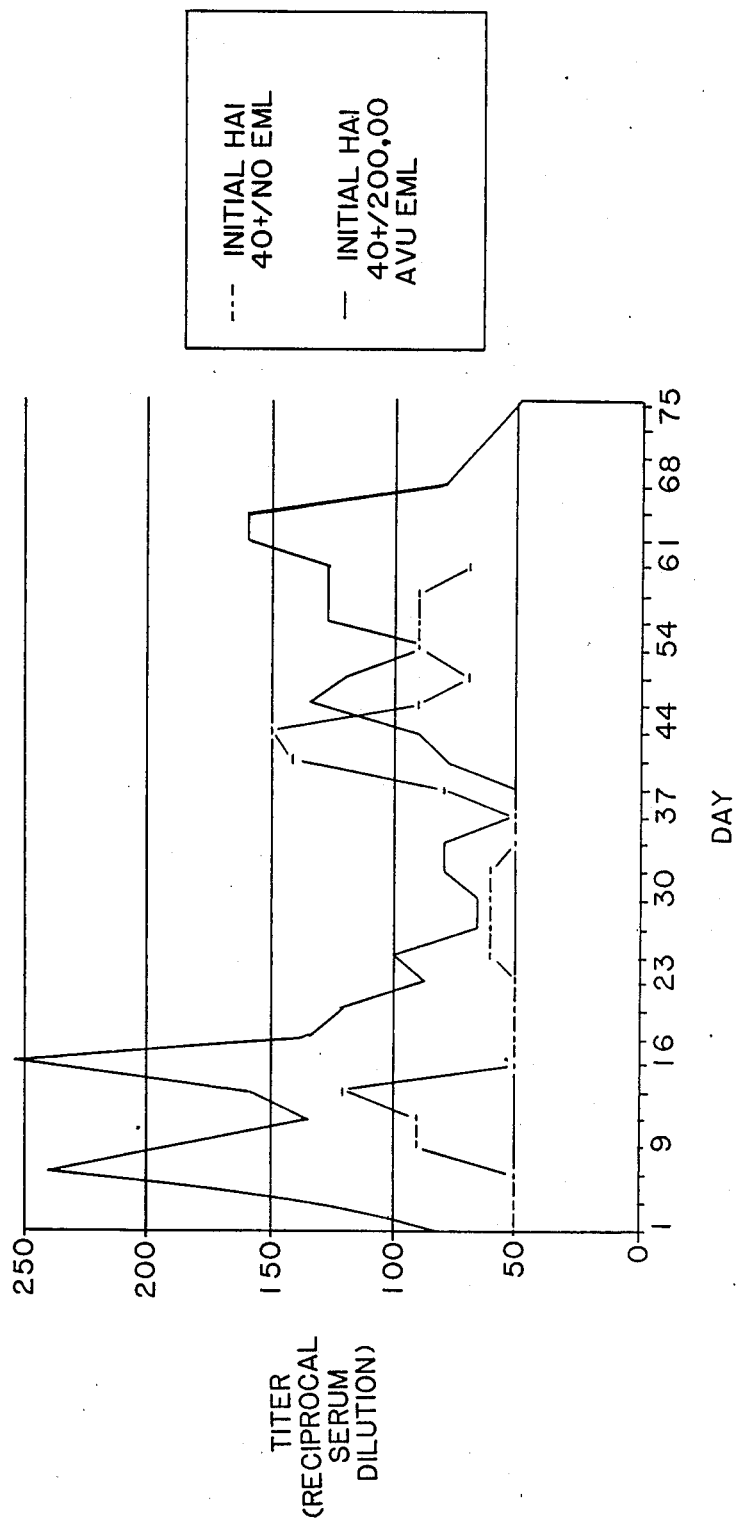
Figure 2:
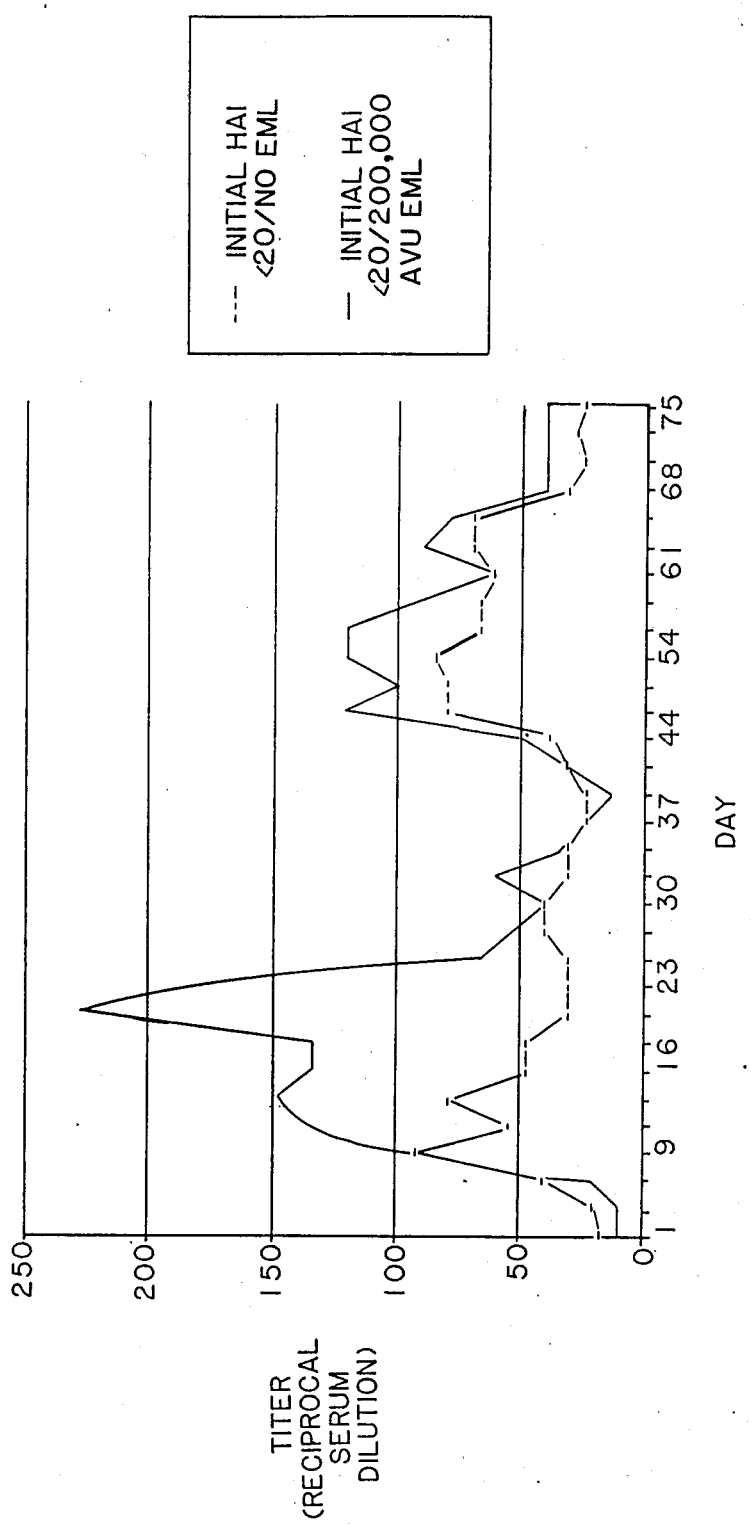
FIG. 2 is a graph showing the same separate and concurrent coadministration as in the graph FIG. 1, i.e. (1) 1350 IPU (200,000 AVU) or (2) no leukokines, except that the equines had a low initial antibody titer of 1:20 or less.
Figure 3:
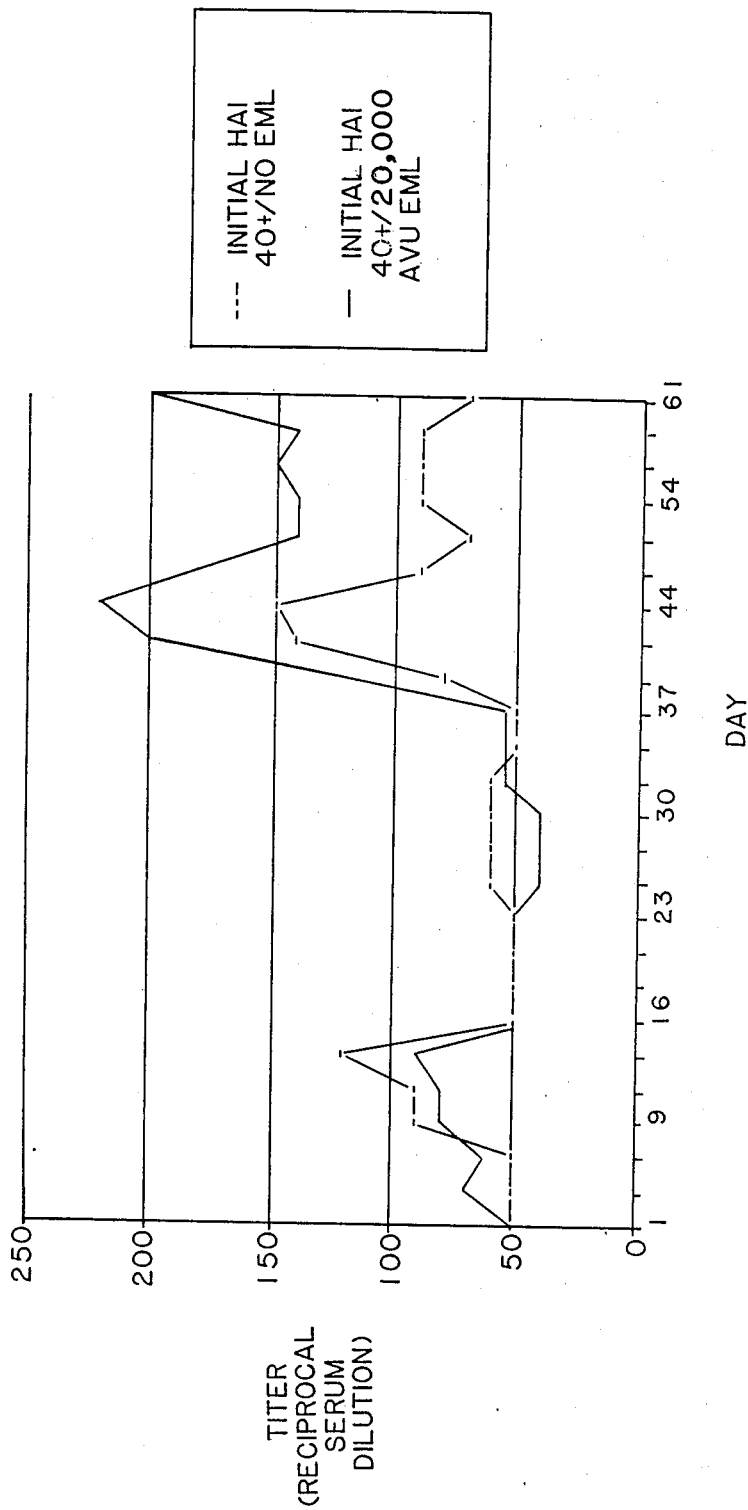
FIG. 3 is a graph showing the same separate and concurrent coadministration as in the graph FIG. 1, except that (1) the leukokines were coadministered with the vaccine at a low level 135 IPU (20,000 AVU) or (2) no leukokines were administered with the vaccine. The equines initially had a high level of serum antibody of 1:60 or higher.
Figure 4:
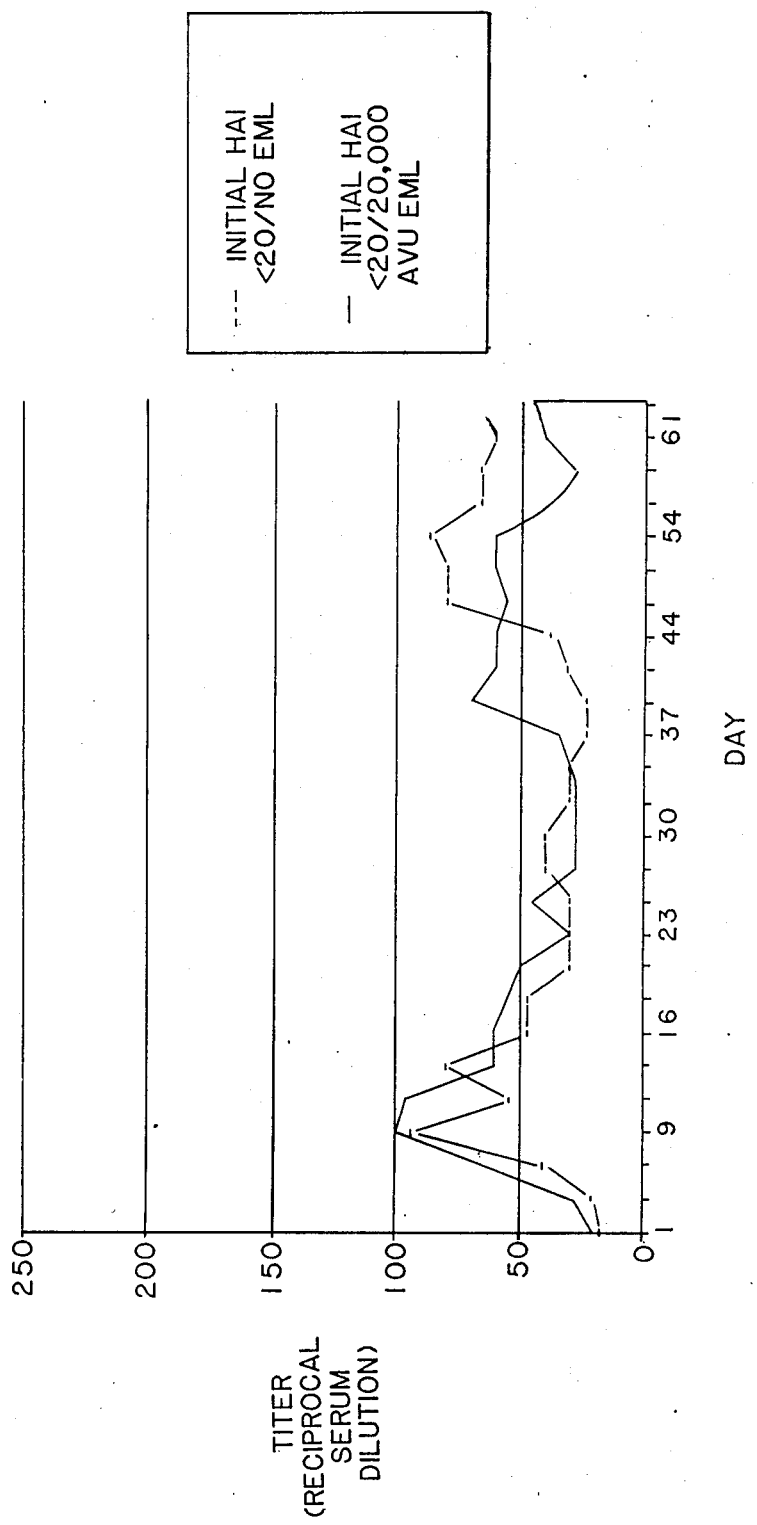
FIG. 4 is a graph showing the same coadministration as in the graph FIG. 2, except that the leukokines were coadministered (1) at a low level 135 IPU (20,000 AVU) or (2) no leukokine was administered. The equines initially had a low level of serum antibody of 1:20 or less.
Figure 5:
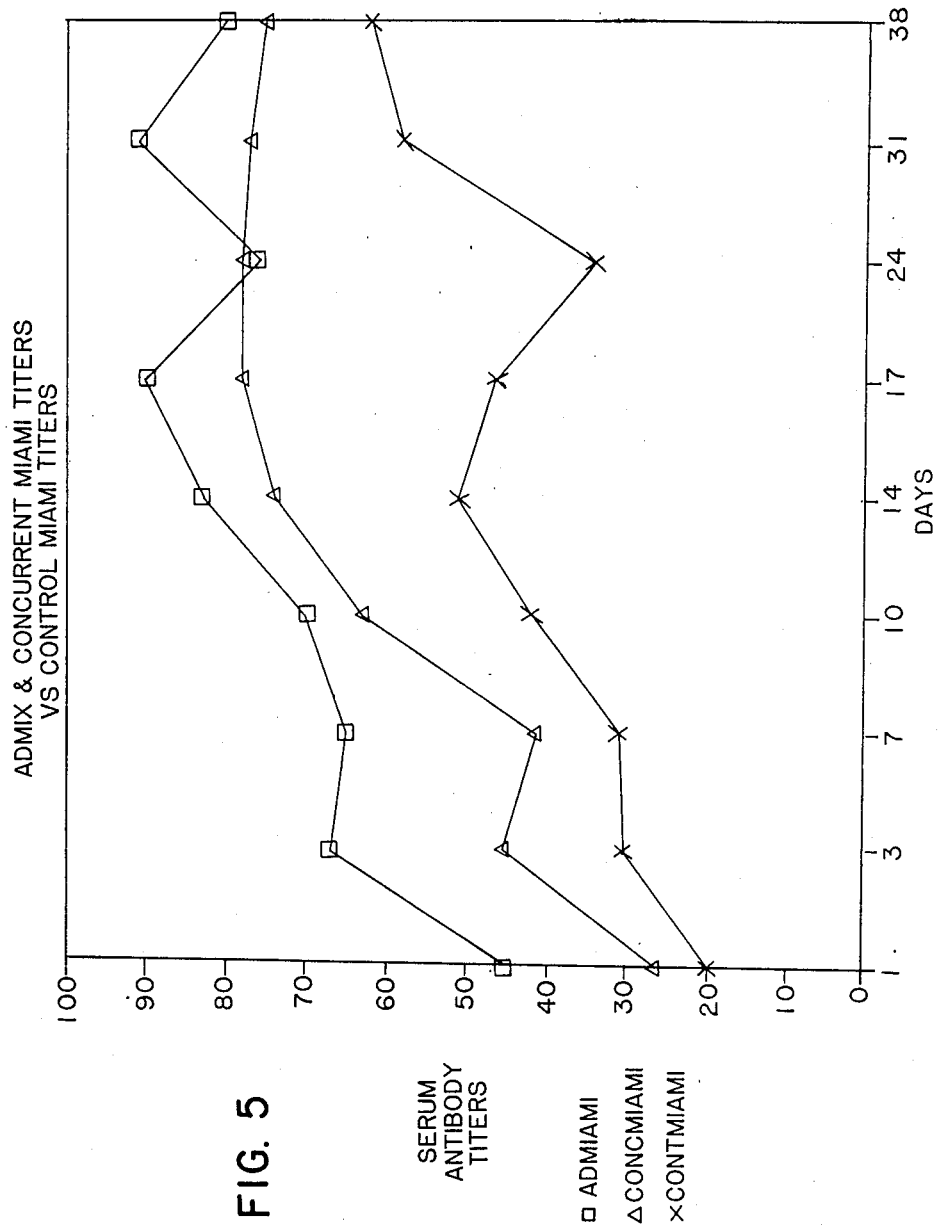
FIGS. 5 to 7 are graphs showing antibody responses in horses for mixed leukokine and vaccines and for concurrently administered vaccines and equine leukokine.
Figure 6:
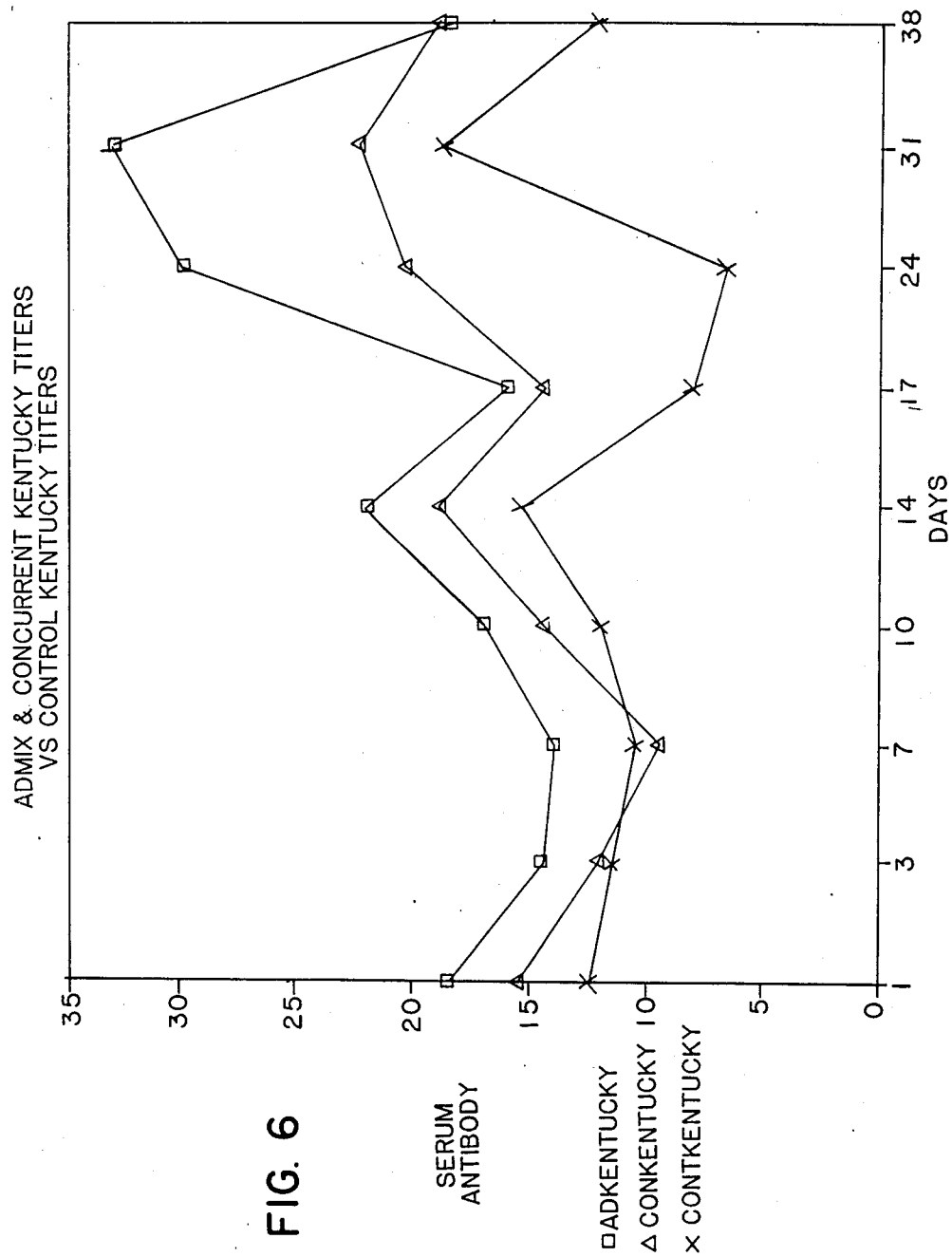

The present invention relates to an improvement in a method for providing an immune response to a disease in a mammal with a viral or viral subunit or other viral antigen vaccine which produces a blood serum antibody response to the vaccine in the mammal which comprises: administering an equine leukokine with the vaccine to thereby provide an enhanced immune response in the mammal. The method particularly relates to the treatment of equine influenza and canine parvovirus.

Further, the present invention relates to a vaccine composition for a mammal which comprises in admixtures: a viral or viral subunit or other viral antigen vaccine which produces a blood serum antibody response to the vaccine in the mammal to provide an immune response to a viral disease; and an equine leukokine as an adjuvant to the vaccine, wherein the leukokine is present in an amount of at least aobut 100 IPU, preferably up to 5,000 IPU, which increases the blood serum antibody response to the vaccine in the mammal. The leukokine generally substantially increases the initial antibody response in the mammals.

The leukokines induced by the virus without purification is mixed with other leukokines of differing molecular size and no attempt is made to purify the leukokines because of the expense; however, this can be done in the manner of U.S. Pat. No. 4,503,035. It is expected that the purified leukokines administered with the vaccine would individually produce more or less antibody response in the equine. It is not believed that the interferons are responsible for the results achieved by the present invention in producing the enhanced antibody response.

The most practical method of producing the leukokines is by virus induction of equine leukocytes in vitro. The preferred virus produces Newcastle disease in chickens. Other viruses which can be used, for instance, are Bluetongue virus, Sindbis virus and Sendai virus. It is generally impractical to isolate the leukokines in vivo. Recombinant genetic techniques can be used to produce the leukokines in bacteria.

The viral, viral subunit or other antigen vaccines are very well known to those skilled in the art. It is especially unexpected that the leukokines would enhance the serum antibody of non-replicating vaccines, such as the equine influenza virus vaccines. The virus are killed by formalin in producing the equine influenza vaccine used in the preferred compositions and method of the present invention. The same results are achieved with canine parvovirus which is a live or replicating virus vaccine and other virus vaccines.

Examples of vaccines where the antibody response in equines can be enhanced are those intended for prophylaxis of viral arteritis; equine encephalomyelitis (Eastern, Western Encephalitis, equine sleeping sickness); equine rhinopneumonitis (herpesvirus type 1); equine abortion (herpesvirus type 3); African horse sickness; and foal gastroenteritis (equine rotavirus). In canines or felines the vaccines can be for rabies, parvovirus, distemper, feline leukemia and adenovirus.

The vaccine compositions can be administered to the mammals in any convenient manner. The most common means is by injection, although nasal sprays and other techniques for blood stream absorption can be used. The vaccines can be separately administered or administered together. The vaccine dosages are usually administered in dosages of 1 ml, usually 0.1 to 5 ml, intramuscularly.

The equine vaccine compositions used are well known to those skilled in the art. U.S. Pat. No. 4,466,957 to Hjorth et al, U.S. Pat. Nos. 4,009,258 and 3,518,347, for instance, describe influenza vaccines. Canine or feline, swine, bovine and other animal vaccines are also well known.

The vaccines can include other conventional adjuvants. These include complete or incomplete Freund's, aluminum hydroxide, peanut oil, by way of example. U.S. Pat. Nos. 3,790,655 and 3,919,411 to Carlson et al describe adjuvants used in the vaccines used in the specific examples.

Preferably the dosage of the leukokine used with the vaccine is betweeen about 20,000 and 1,000,000 Antiviral Units (AVU). One assay for the leukokines used in the present invention uses a human interferon preparation developed by the National Institute of Health as a reference standard as discussed herein. This assay uses the interferon as an indirect measure of the activity. Also the level of antibodies developed by murines are used as an assay with a particular vaccine. Generally, between about 0.1 and 10 milligrams of lyophilized, powdered leukokine mixed with water (0.5 to 1 ml) is used per cc of vaccine as an adjuvant. The amount of leukokine used depends upon the immunopotency of a particular lot, usually in mice as the least expensive test animal.

In particular, equine mixed leukokines (EML), when administered separately intramuscularly along with a formalin-inactivated combined equine (influenza) virus vaccine, cause an increase of humoral immune antibody response to the vaccine antigen in equines. The EML are produced by induction of isolated equine leukocytes with Newcastle disease virus in vitro. The EML were extracted and partially purified by diafiltration and ultrafiltration but the induced leukokines are not isolated. The increase in antibodies reactive with the vaccine antigens occurs more rapidly and is of greater magnitude with the leukokines than the antibody response from the vaccine alone. This translates to a greater assurance of protection against equine (influenza) virus or other virus vaccine, with the resultant economic and practical benefits of realizing that protection from fewer vaccinations.

SPECIFIC DESCRIPTION

A. Process of Producing Equine Mixed Leokokines (EML).

1. Collection and Prepartion of Equine Leukocytes.
    a. Equine peripheral blood leukocytes were collected by a process of leukophoresis in which up to 15 L or peripheral blood from a single animal were subjected to processing. The peripheral blood leukocytes were retained and the red blood cells and plasma returned to the animal.
    b. The volume of the peripheral blood leukocytes obtained was assessed in an appropriate vessel and the cells were diluted to a volume three times the starting volume with cold Tris-HCl buffered ammonium chloride (140 mM $NH_4Cl$, 6 mM Tris-HCl), pH 7.4, to initiate the elimination of any remaining red blood cells.

c. After five minutes incubation at room temperature, with frequent agitation, the cell suspension was centrifuged at 500×g for 15 minutes at 4 degrees Centigrade.

d. The cell pellet was resuspended in a minimal amount of Hank's Balanced Salt Solution without $Ca^{2+}$ and $Mg^{2+}$ (HBSS), pH 7.4, and centrifuged at 500×g for 15 minutes at 4° C.

e. Following a subsequent wash with HBSS, pH 7.4, the cells were resuspended in a known volume of HBSS.

f. A portion of the cell suspension was diluted 1:20 with HBSS and the total number of cells estimated by hemocytometer count.

g. Cells in the original suspension were pelleted by centrifugation at 500×g for 15 minutes at 4 degrees C. and resuspended in nutrient medium to result in a final concentration of 1×10 (7) cells /ml.

2. Preparation of Newcastle disease virus (NDV) for Induction, and Determination of Hemagglutination Titer.

a. NDV (strain B1, Hitchner; ATCC VR-108) was inoculated into the allantoic cavity of 10 day embryonated eggs, and allantoic fluid containing virus was harvested after a further 72 hour incubation. The allantoic fluids were pooled so as to result in several lots.

b. Freshly drawn chicken blood was mixed 1:1 with cold Alsever's solution (0.42% NaCl, 0.8% trisodium citrate, 2.05% glucose, 0.055% citric acid, pH 7.4) and centrifuged at 500×g for 15 minutes.

c. Serum and Alsever's solution were decanted and discarded.

d. Cells were resuspended in Alsever's solution, mixed throughly, and centrifuged at 500×g for 15 minutes.

e. Resuspension of cells, centrifugation, and decantation were repeated.

f. From the packed cell volume, a 0.5% suspension of the chick red blood cells (CRBC) was made in PBS.

g. To each of twelve (12) consecutive wells of a 96 well microtiter (V-shaped wells) was added 0.1 ml PBS.

h. 0.1 ml of allantoic fluid from a single lot was added to the first well.

i. Serial 2-fold dilutions were made by transferring 0.1 ml of each consecutive dilution out through well 12.

j. 0.1 ml of the 0.5% CRBC suspension was added to each well.

k. The above procedure was followed for every lot of NDV-containing allantoic fluid in the current pool.

l. 0.1 ml of the 0.5% CRBC suspension was added to 3 wells containing only 0.1 ml PBS (negative control wells).

m. Hemagglutination was assessed when CRBC's in the control wells form "buttons" in the bottom of the wells (the "buttons" ran when the plate was slightly tilted). The titer was equal to the reciprocal of the highest dilution which interferes with "button" formation of the control type, expressed in hemagglutinating units/ml (HAU/ml).

n. Individual lots from the current pool of allantoic fluid which showed the highest HAU/ml were pooled for induction.

o. The induction pool was dispensed such that each aliquot contains enough NDV for 3 to 5 liters of nutrient induction medium, based on a final 15 HAU/ml. Aliquots were stored at −70 degrees Centigrade until use.

3. Preparation of Nutrient Medium for Leukocyte Culture.

a. The nutrient medium for maintenance of the isolated equine peripheral blood leukocytes in which the cells were induced to produce EML, was similar to that described by N. N. Iscove and F. Melchers. (J. Exp. Med 147:923–933, 1978), with the modifications specified below:

1. Iscove's Modification of Dulbecco's Modified Eagle's Medium (IDMEM; Gibco, Grand Island, N.Y.) was rehydrated according to package directions.

2. Addition was made of alpha-thioglycerol (Sigma, St. Louis, MO.) to a concentration of 75 mcM, in nutrient medium.

3. An emulsion of soybeam lecithin (type II-S; Sigma) was made in 100 ml of Dulbecco's Modified Eagle's Medium (DMEM) also containing 10 mg/ml fatty acid-free bovine serum albumin (FAF-BSA; Sigma), pH 5.0, by trituration and homogenization of 750 mg of lecithin and including it in the final 10 ml of DMEM—BSA. This mixture was filtered through a sterile 0.45 micron membrane (millipore) before addition to the nutrient medium to achieve the final concentrations of lecithin (75 mcg/ml) and BSA (100 mcg/ml).

4. Fetuin (Spiro method, Gibco) was sometimes added to the nutrient medium to achieve final concentration of 150 mcg/ml. It was found that this step was unnecessary for immunopotentiating activity.

5. Transferrin (Gibco), 4 mg/ml was ⅓ saturated by the addition of 296 nmol $Fe(NO_3)_3$, passed through a 0.2 micron filter (millipore, Bedford, MA), and added to the nutrient medium to a final transferrin concentration of 1 mcg/ml.

4. Induction of Equine Leukocytes for Production, and Recovery of the EML.

a. The washed equine leukocytes were suspended in the complete nutrient medium at a final concentration of $1\times10^7$ cells /ml in the induction vessel (BioCul Type 20 Cell Culture System; Queue Systems, Parkersburg W.V.). To this cell suspension were added EML, previously induced, purified and concentrated by this procedure, to a final concentration of 50 AVU/ml of nutrient medium.

b. The contents of the induction vessel were gently stirred in a constant temperature waterbath (37° C.) for 5 hours. During this and the subsequent incubation, the pH was monitored by an internal probe and adjusted to pH 7.4 by automatic addition of acid or base.

c. After 5 hours of incubation, allantoic fluid grown Newcastle disease virus (NDV) was added to a final concentration of 15 HAU/ml. The HAU of the NDV pool had previously been assayed by standard methods (Sec. 2 above).

d. Incubation was continued for 18 to 20 hours at 37° and pH 7.4 with gentle stirring to maintain the cells in suspension.

e. The contents of the induction vessel were transferred aseptically to sterile centrifuge bottles and centrifuged at 1500×g 30 minutes at 4° C. The cell pellet was discarded.

f. A sample of the supernatant was taken for centrifugation at 100,000×g for 1 hour before assay for antiviral activity by the plaque reduction method described hereinafter. The balance was held at −20° C. until processing.

5. Diafiltration, Ultrafiltration and Concentration of EML.

a. Supernatant collected from the induction vessel was diafiltered using an Amicon DC 10L ultrafiltration unit fitted with a 100,000 MW cut-off hollow fiber cartridge (H5p100-43; Amicon Corp., Danvers, MA). Prior to diafiltration the cartridge was cleaned and equilibrated by sequentially running through the unit:
1. Five liters of 0.2 M NaOH for 20 minutes,
2. Five liters of distilled $H_2O$ for 2 rinses of 20 minutes each,
3. Two liters of phosphate buffered saline (0.8% NaCl, 0.02 KCl, 0.12% $Na_2HPO_4$, 0.02% $KH_2PO_4$; PBS), pH 9.0, containing 0.5% fraction V albumin, for 20 minutes,
4. Two liters of 5 mM sodium phosphate buffer, pH 7.4, for 20 minutes.

After loading the supernatant, diafiltration was initiated with 6 to 7 volumes of 5 mM sodium phosphate buffer, pH 7.4, which resulted in reduction of the reservoir volume to approximately 500 ml. Samples were removed for assay of antiviral activity and to determine absence of presence of live virus.

b. Following decontamination of the ultrafiltration unit by a 20 minute rinse with 5 L of 0.2 N NaOH, it was next fitted with a hollow-fiber cartridge with a 10,000 MW cut off limit (H10P10-20) and steps (2) through (4) of 5.a above were repeated.

c. The diafiltrate was ultrafiltered and concentrated against the 10,000 MW hollow fiber cartridge to approximately 500 ml.

d. The remaining crude EML product was removed from the reservoir, filter sterilized by use of a 0.2 micron filter apparatus (Millipore), distributed to sterile vials, and lyophilized.

e. Contents of random vials were taken for assessment of sterility, antiviral activity, protein content, and other biochemical characterizations.

6. Plaque Assay for Antiviral Activity of EML.
a. Viral plaque reduction assay was performed as described by Langford, et al. (Methods in Enzymology, V. 78, Academic Press, New York, New York, p. 339, 1981), utilizing monolayers of equine dermal fibroblasts (E. Derm, ATCC-CCL57) challenged with Vesicular Stomatitis virus.
b. In this assay, utilizing WISH human amniotic cells, NIH Reference Human Interferon Alpha (HuIFN-alpha[Leukocyte/Sendai]Ga23-902-530), having an assigned potency of 4.08 log 10 International Units (IU)/ml, demonstrates 4.59 log 10 IU/ml.

B. Use of EML to Augment the Humoral Immune Response to Commercially Available Killed Equine Influenza Virus Vaccine.
1. The EML, produced as described above, were reconstituted from the lyophilized stat with sterile distilled water so as to result in an injection volume of 1 to 5 ml containing 135 to 1350 IPU (20,000 to 200,000 AVU) of antiviral activity for intramuscular administration to the animals.
2. At the time of vaccination with the commercial available formalin-inactivated equine influenza virus vaccine, the EML were separately co-administered by intramuscular injection. Subcutaneous injection could also have been used.
3. Humoral antibody resonses of animals after injection with the vaccine alone or with EML injection were assessed by standard hemagglutination inhibition (HAI) tests as modified from Hierholzer, J. C., Suggs, M. T., and Hall, E. C. (Appl. Microbiol. 18:824–833, 1969) as adapted for the microtiter method, using as antigen allantoic fluid-grown influenza viruses of the same prototype strains as used in the equine vaccine (currently these are A/equi-2/Miami/1/63 and A/equi-1/Prague/1/56).
a. Equine sera for assay were pretreated and diluted as follows:
1. To 0.5 ml serum was added 2.0 ml borate-buffered saline (0.7% NaCl, 0.3% $H_3BO_3$, 0.01% NaOH; BBS), pH 9.0, and 2.5 ml of a 25% suspension of acid-washed kaolin (Sigma) in BBS, pH 9.0.
2. The solution was shaken vigorously at 5 minute intervals for 20 minutes at 24 degrees Centrigrade.
3. The solution was centrifuged at 800×g 30 minutes.
4. The supernatant was decanted to separate tubes. This represents a 1:10 dilution of original serum.
5. The diluted serum was inactivated at 56 degrees Centigrade for 30 minutes.
b. The hemagglutination inhibition (HAI) test was run as follows using 96 well microtiter trays:
1. 25 mcl PBS was added to wells 2 through 12 of rows designated for serum dilutions. 2. 50 mcl PBS added to 3 wells for cell controls, and to 6 others for virus "back-titration".
3. 50 mcl of each of the starting serum dilutions (1:10) was added to the first wells of each of two rows in which serum dilutions will be made.
4. Serial 2-fold dilutions of the sera by transfer of 25 mcl were made to each well out through well 12 of each row.
5. 25 mcl of PBS was added to all wells of every second row (these were serum control wells).
6. The appropriate allantoic fluid-grown influenza virus in PBS were diluted such that 0.1 ml contains 16 HAU of activity (Sec. 8.A.2., determination of HAU).
7. 25 mcl (4 HAU) of the virus dilution were added to all wells of the remaining rows which contain serum dilutions (these are the serum antigen wells).
8. 50 mcl of the virus dilution were added to the first of the wells for antigen "back-titration".

9. Further serial 2-fold dilutions of the virus dilution were made by transfer of 50 mcl to each well through well 6.
10. The plates were shaken carefully and incubated at 24 degrees Centigrade for 30 minutes.
11. 50 mcl of a 0.5% suspension of CRBC's (Sec. 8.A.2.b-f) were added to all wells.
12. The plates were shaken carefully, and incubation continued.
13. The plates were read for HAI when the cell control wells showed compact "buttons". Cell control "buttons" ran when the plate was titled, as should any HAI-positive wells (those where hemagglutination had been inhibited by antibody). HAI-negative wells show an even distribution of CRBC over the bottom of the wells. The HAI titer of the serum was expressed as the reciprocal of the serum dilution (starting dilution is 1:10) in the last well to show a "button" (no hemagglutination).
14. Serum control wells should not show hemagglutination (auto-agglutination); any auto-agglutination may mask low serum antibody titers.
15. Virus "back-titration" should indicate the presence of 4 HAU/25 mcl. Typically, the first 3 wells will show hemagglutination, the last 3 wells will "button".

EXAMPLE 1

Figure 8:
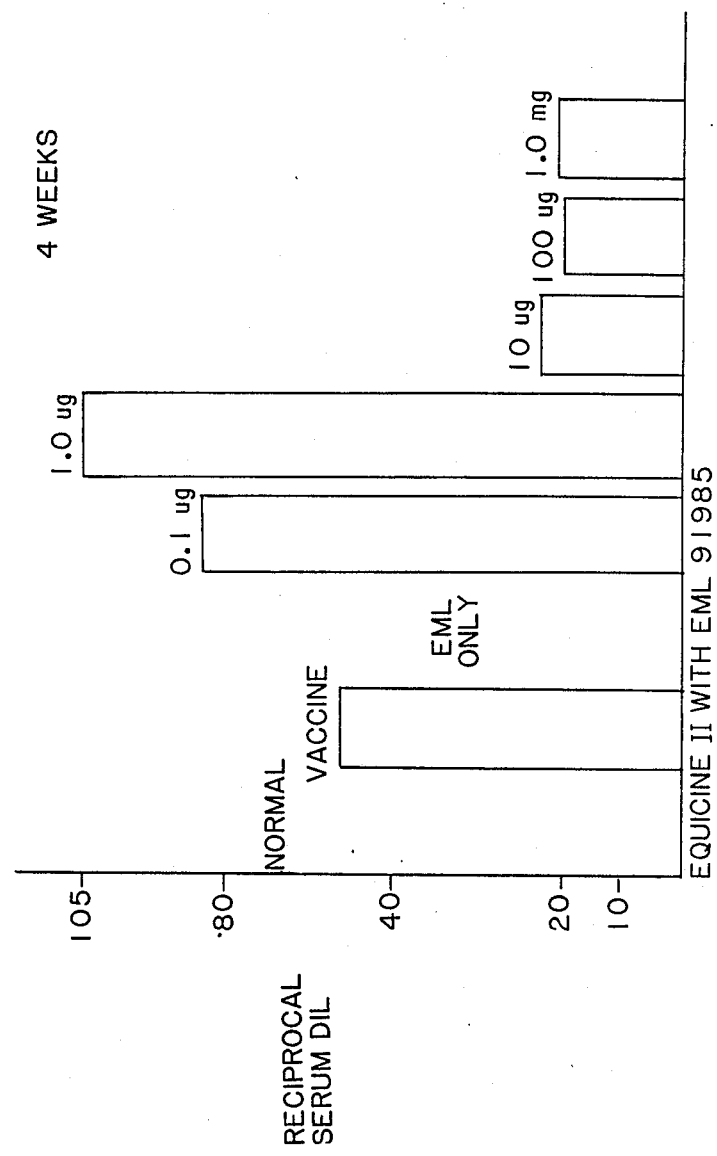
Figure 9:
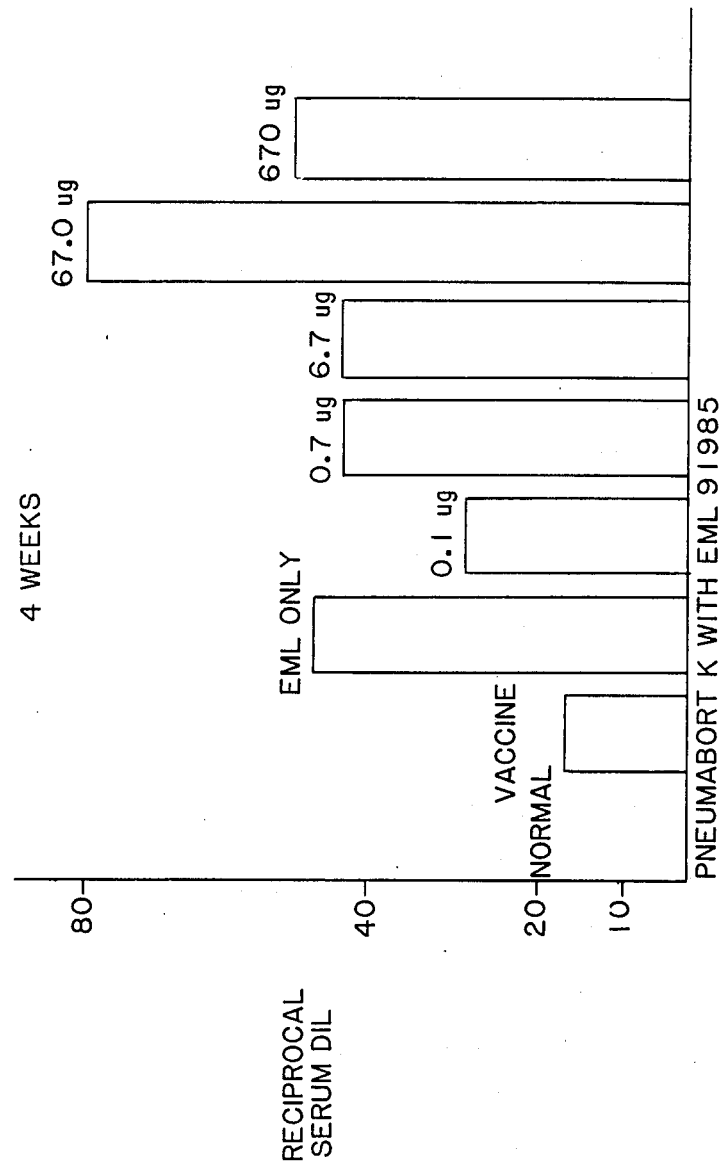

At the time of vaccination of an equine with killed equine influenza virus vaccine, 20,000 to 1,000,000 AVU of EML was also administered intramuscularly, preferably 200,000 to 400,000 AVU. FIGS. 1 to 4 show the results of the vaccination. The results are quite pronounced where the equines had higher levels of the antiflu antibody initially. Administration of higher levels of leukokines also produced improved results. As shown in the Figures the equines were revaccinated at day 31 to 34. The influenza vaccine was in a dosage of 1 ml.

FIGS. 1 to 4 show vaccinations as follows:

HAI LO Group: serum titer 1:20 or less to A/Equi-2/Miami/1/63 at start of study.
- Vaccinate+EML (200,000 AVU antiviral activity)
- Vaccinate+EML (20,000 AVU antiviral activity)
- Vaccinate−EML (control group)

HAI HI Group: serum titer 1:60 or higher to A/Equi-2/Miami/1/63 at start of study)
- Vaccinate+EML (200,000 AVU antiviral activity)
- Vaccinate+EML (20,000 AVU antiviral activity)
- Vaccinate−no EML (control group)

Three equines were used per group. The EML equines receive EML on two occasions (when vaccinated). Blood is drawn every second day for about 70 days. All equines received the second vaccination with-/without EML on approximately day 33. Serum anti-flu titer in FIGS. 1 to 4 refers to the reciprocal of the serum dilution resulting in inhibition of erythrocyte agglutination.

EXAMPLE 2

Thirty (30) standard bred mares at a local horse farm were randomly assigned to three test groups of ten (10) animals each. The mares had all been kept on a strict influenza vaccine regiment consisting of vaccination at eight week intervals. The animals were not pre-sorted on the basis of HAI titers. In one group (Admix), 3.35 mg (3350 IPU; 500,000 AVU) of EML in 1.0 ml sterile distilled water was admixed with influenza vaccine (Equicine II) in the same syringe and administered intramuscularly in the neck. In another group (Concurrent), the vaccine was administered on one side of the neck and 3.35 mg (3350 IPU; 500,000 AVU; EML in 1.0 ml sterile distilled water was given concurrently on the opposite side of the neck. Both injections were intramuscular. The remaining group (Control) received vaccine only.

All animals were bled prior to vaccination and/or administration of EML, then twice weekly thereafter for a total of 38 days. HAI titers to the equine influenza virus antigens contained in the bivalent vaccine, as well as to A/Equi-2/Kentucky (ADKENTUCKY, CONCKENTUCKY and CONTKENTUCKY), were determined as described above. As the results graphically rendered in FIGS. 5 to 7 show, there was an immunoenhancement of HAI antibody to both A/equi-2/Miami/1/63 (FIG. 5), and to A/equie-2/Kentucky/1/81 (FIG. 6), especially during the later part of the test period, in animals receiving EML admixed (AD) or concurrently (CONC) with vaccine. The latter strain is not included in the vaccine, but represents a more recent field isolate. The results may therefore indicate an enhanced protection against cross-reacting virus strains. The enhancement was significant at $p<0.05$ by two-tailed Student's t-test, and by an angular transformation analysis designed to ameliorate the effect of disparate initial HAI titers. The response of the animals to A/equi-1/Prague (ADPRAGUE, CONCPRAGUE and CONTPRAGUE; FIG. 7) proved not to be statistically significant. This may have been due in part to the generally high levels of HAI titers to this strain initially and the difficulty in discriminating titer changes.

EXAMPLE 3

C. Mouse Test for In vivo Immunopotentiation by EML.

1. Immunization.
   a. Groups of Balb/c mice were immunized with 0.5 ml of an inactivated equine influenza virus vaccine, Equicine™ (Haver-Lockhart; Bayvet Div., Miles Labs, Elkhart Indiana). Further examples were, an inactivated equine rhinopneumonitis virus vaccine, Pneumabort K™ (Fort Dodge Labs), or a modified live canine Parvovirus vaccine, Vanguard CPV™ (Norden Labs), at a final dilution of 1:10 in phosphate buffered saline (PBS), with or without EML. Equicine II™ and Pneumabort K™ were given admixed with EML as intraperitoneal injections. Vanguard CPV™ was given concurrently with EML, 0.25 ml of each subcutaneously in each flank.
      1. Control group (2 animals) was given vaccine only 0.25 ml vaccine at 1:5 dilution plus 0.25 ml PBS).
      2. Experimental groups (3 animals each) were given EML at several serial ten-fold dilutions, starting at a leukocyte protein concentration of 1.0 mg/0.25 ml, plus vaccine (0.25 ml EML dilution plus 0.25 ml vaccine dilution at 1:5).
      3. A group of 2 animals received EML only at the lowest dilution used for the experimental groups.
   b. Animals were bled at 2 or 4 weeks post-injection and sera obtained.

c. Antibodies toward vaccine antigens were determined using standard indirect ELISA technique and utilizing whole vaccine adsorbed to polystyrene microtiter plates.
2. Determination of Optimum Antigen Dilution for ELISA.
   a. Microplates (96-well) were coated using serial 2-fold dilutions of Equicine II ™ or Pneumabort K ™ in carbonate-bicarbonate buffer, pH 9.8 or Vanguard CPV ™ in PBS, pH 7.4.
   b. Wells were screened for activity against several dilutions (in PBS) of normal mouse serum (not exposed to the antigen in question) and mouse serum known to contain anti-vaccine antibody.
   c. The last dilution of vaccine antigen yielding an absorbance ratio of 2.0 with a 1:160 dilution of the appropriate standard serum was used as the optimal antigen concentration for the titration studies to determine EML immunopotentiating activity in mice. For both Equicine II ™ and Pneumabort K ™, the optimal antigen concentration for adsorption to assay plates was achieved at a 1:8 dilution of vaccine. For Vanguard CPV ™, optimal antigen concentration was at 1:16 dilution of vaccine.
3. Indirect ELISA.
   a. Preparation of ELISA plates.
      1. To each well of the multiwell assay plate was added 50 microliters of the predetermined vaccine dilution (in PBS, pH 7.4, or in bicarbonate-carbonate buffer, pH 9.5)).
      2. Incubation was carried out at 4° C. overnight.
      3. Antigen removed by inverting and "flicking" plates.
      4. Two Hundred microliters of PBS-1% BSA, pH 7.4 was added to each well.
      5. Incubation was carried out for 2 hours at room temperature.
      6. Buffer was removed by "flicking" plate.
      7. Unused plates were stored at −20° C. until use.
   b. Immunoassay and Substrate Development.
      1. Fifty microliters of a 1:10 dilution of test mouse serum in PBS was added to the first well of a series and diluted out in PBS by serial two-fold dilutions.
      2. Incubation was carried out for 90 minutes at room temperature.
      3. Wells were washed 2 times with PBS-1% BSA, pH 7.4.
      4. Fifty microliters of alkaline phosphatase-conjugated rabbit anti-mouse IgG was added to each well (approximately 1:1000 dilution in PBS-1% BSA, to be determined experimentally).
      5. Incubation was continued for 1 hour at room temperature.
      6. Conjugated antibody was removed, and wells washed 2 times with PBS-1% BSA, pH 7.4.
      7. Wells were washed once with double-distilled water.
      8. Fifty microliters of alkaline phosphates substrate was added to each well (1 mg p-nitrophenylphosphate/ml of 1.0 M diethanolamine-0.02% sodium azide, pH 9.0).
      9. Incubation was continued for 30 minutes at room temperature.
      10. Color development in each well was read spectrophotometrically at 405 nm.
      11. The reciprocal dilutions of each test serum resulting in half-maximal binding (as measured by $OD_{405}$) were determined from the titration curve of log reciprocal serum dilutions versus $OD_{405}$, and gave a measure of antibody level to vaccine antigens in the test sera. Values from duplicate or triplicate determinations were averaged to generate the titration curves. The dose of EML resulting in the great enhancement of anti-vaccine antibody was thus determined. The results are shown in FIGS. 8 to 10.

TABLE 1

| | Anti-Equicine II ™ Antibody* at 4 weeks post-injection |
|---|---|
| Vaccine only | 60* |
| EML only (lot #91985) | <10 |
| Vacc. + 0.0001 mg EML | 85 |
| Vacc. + 0.001 mg EML | 105 |
| Vacc. + 0.01 mg EML | 15 |
| Vacc. + 0.01 mg EML | 21 |
| Vacc. + 1.0 mg EML | 22 |

*Reciprocal titer at 50% antigen-antibody binding.

TABLE 2

| | Anti-Pneumabort K ™ Antibody at 4 weeks post-injection |
|---|---|
| Vacc. only | 17* |
| EML only (lot #91985) | 50 |
| Vacc. + 0.067 mcg EML | 30 |
| Vacc. + 0.67 mcg EML | 46 |
| Vacc. + 0.7 mcg EML | 46 |
| Vacc. + 67 mcg EML | 80 |
| Vacc. + 670 mcg EML | 53 |

*Reciprocal titer at 50% antigen-antibody binding.

TABLE 3

| | Anti-Vanguard CPV ™ Antibody at 2 weeks* |
|---|---|
| Vacc. only | 39 |
| EML only (lot #91985) | <10 |
| Vacc. + 1 mcg EML | 72 |
| Vacc + 10 mcg EML | 63 |
| Vacc + 100 mcg EML | 50 |

*Reciprocal titer at 50% antigen-antibody binding; 2 weeks was peak activity for Vanguard CPV ™ (MLV).

Figure 7:
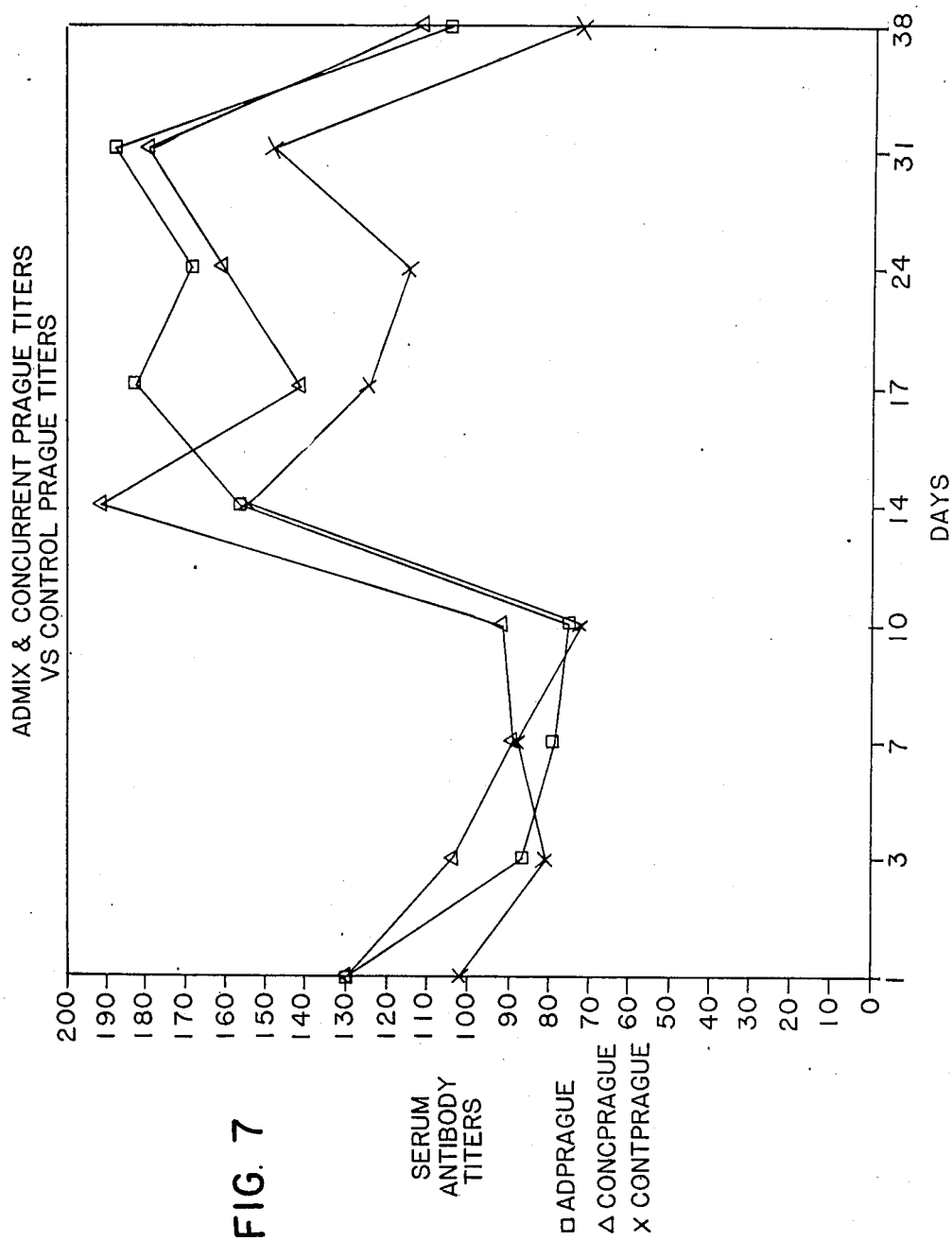

The murine antibody response can serve as a basis for testing the response of the various leukokine and vaccine mixtures for potency. For Example, results of Table 1 indicate that in the case of Equicine II ™, EML lot #91985 shows 1 mouse immunopotentiating unit (IPU) equal to 1.0 mcg; on the other hand, the same lot of EML with Pneumabort K ™ shows 1 IPU equivalent to 67 mcg (Table 2). Table 3 and FIG. 7 show the results with canine parvovirus Vanguard CPV ™ at two (2) weeks post injection. Thus separate lots of leukokine and/or leukokine and vaccine mixtures can be standardized in mice. This is a much more direct and reliable method for measuring potency since it is directly related to the activity of the leukokines. The test for interferon also measures potency of the EML but appears to be measuring a component (interferon) not directly related to the responses claimed because of the effectiveness of the leukokines with non-replicating vaccines.

EXAMPLE 4

D. Use of EML to Augment the Humoral Immune Response of Dogs to Commercially Available Modified Live Canine Parvovirus Vaccine.

1. The EML, produced as described above, were reconstructed from the lyophilized state with sterile distilled water so as to result in an injection volume of 0.5 to 1.0 ml containing 0.067, or 1.34 mg (67, or 1340 IPU, respectively) of leukokine protein for intramuscular administration to the animals. A second study utilized similar injection volumes containing either 0.34 or 1.34 mg (340 or 1340 IPU, respectively).

2. Puppies selected for the study were littermates, weaned at 4-4 and a half weeks, free of parvovirus and canine distemper, and had been screened for levels of maternal anti-parvovirus antibody by hemagglutination inhibition test at least 2 weeks previous to vaccination.

3. At the time of vaccination in the right thigh with a commercially available modified live parvovirus vaccine (Vanguard CPV ™ (MLV), Norden Laboratories, Inc.) the EML at either dosage level were separately co-administered by intramuscular injection of the opposite thigh.

4. Animals were bled at regular intervals and sera obtained. Titers of circulating anti-parvovirus antibody were obtained by standard hemagglutination inhibition (HAI) as previously described herein and virus neutralization tests according to standard methods (Diagnostic Procedures For Viral and Rickettsial Diseases, 5th ed., American Public Health Association, New York, 1981). All dogs were given a second dose of vaccine 40 days after the first injection, and another dose of EML if indicated. Blood samples for serum were collected weekly for an additional 3 weeks after the second dose of vaccine.

5. The results of the filter dog study are shows in Tables 4 and 5. It can be seen that the only dogs responsive to the first dose of MLV CPV vaccine were the two that also received 1.34 mg (1340 IPU) of EML. While the lack of interfering maternally-derived antibody (SN titer <2) in one of these animals is the probable reason it responded better than any of the other dogs, its duplicate had the greatest level of maternal antibody at the time of first vaccination and yet it developed the highest titer post-vaccination.

There were no differences in antibody responses of the two control dogs and the two receiving 0.067 mg (67 IPU) EML. All four failed to respond to the first dose of vaccine, but all four responded to the second dose of vaccine. The low levels of SN antibody at the time of the first dose of vaccine may have ameliorated the response to the vaccination as seen in the case of these four animals. The immunopotentiating activity of EML, however, is evident at the higher dosage where it promoted a higher level of protective antibody to replicating parvovirus earlier in life and with a single immunization.

The data tabulated in Tables 6 and 7 show again the efficacy of the 1.34 mg (1340) IPU) dose of EML in bringing up HI and SN titers to canine parvovirus vaccine higher and more rapidly than vaccination alone. The results of a 0.34 mg (340 IPU) dose of EML were less dramatic, but the SN titers were moderately elevated at an earlier time than those of the control animals.

TABLE 4

Effect of EML on Antibody Response to MLV CPV: Hemagglutination-Inhibition (HAI) Test Results Titer of HI antibody to CPV in serums collected on dates

| Treatment Group | Dog No. | Day 1 * | Day 7 | Day 13 | Day 16 | Day 23 | Day 35 ** | Day 41 | Day 48 | Day 53 |
|---|---|---|---|---|---|---|---|---|---|---|
| MLV CPV | 8601 | <20 | <20 | <20 | <20 | <20 | <20 | 80 | 80 | 20 |
| only | 8606 | <20 | <20 | <20 | <20 | <20 | <20 | 160 | 160 | 160 |
| MLV CPV | 8602 | <20 | <20 | <20 | <20 | <20 | <20 | 40 | 40 | 20 |
| EML 0.067 mg | 8603 | <20 | <20 | <20 | <20 | <20 | <20 | 160 | 160 | 80 |
| MLV CPV | 8604 | <20 | 20 | 160 | 80 | 160 | 320 | 640 | 160 | 160 |
| EML 1.34 mg | 8605 | <20 | <20 | 20 | 80 | 320 | 160 | 640 | 320 | 640 |

*Date of first vaccination;
**date of second vaccination

TABLE 5

Effect of EML on Antibody Response to MLV CPV: Serum-Virus Neutralization (SN) Test Results Titer of SN antibody to CPV in serums collected on dates

| Treatment Group | Dog No. | Day 1 * | Day 7 | Day 13 | Day 16 | Day 23 | Day 35 ** | Day 41 | Day 48 | Day 53 |
|---|---|---|---|---|---|---|---|---|---|---|
| MLV CPV | 8601 | 2 | 2 | 4 | 2 | 2 | 4 | 64 | 64 | 64 |
| only | 8606 | 2 | 4 | 2 | <2 | 2 | 8 | 1024 | 512 | 256 |
| MLV CPV | 8602 | 2 | <2 | <2 | <2 | <2 | <2 | 32 | 16 | 16 |
| EML 0.067 mg | 8603 | 2 | 4 | 2 | < | 2 | 4 | 512 | 256 | 256 |
| MLV CPV | 8604 | <2 | 64 | 512 | 512 | 1024 | 512 | 1024 | 1024 | 512 |
| EML 1.34 mg | 8605 | 4 | 8 | 4 | 4 | 4096 | 2048 | 4096 | 4096 | 4096 |

*Date of first vaccination;
**date of second vaccination.

TABLE 6

Antibody Response to MLV Canine Parvovirus Vaccine - HI Titers.
The Effect of Equine Mixed Leukokine on Antibody Response to Modified Live
Virus Canine Parvovirus Combination Vaccine: Hemagglutination-Inhibition (HI) Titers

| Treatment Group | Dog No. | 2/07* | 2/14 | 2/21 | 2/28 | 3/07** | 3/14 | 3/21 | 3/28 |
|---|---|---|---|---|---|---|---|---|---|
| EML only | 8606 | <10 | <10 | <10 | <10 | <10 | <10 | <10 | <10 |
| (200K AVU) | 8614 | <10 | <10 | <10 | <10 | <10 | <10 | <10 | <10 |
| 1340 IPU | 8618 | <10 | <10 | <10 | <10 | <10 | <10 | <10 | <10 |
| Geometric mean | | <10 | <10 | <10 | <10 | <10 | <10 | <10 | <10 |
| Vaccine only | 8611 | <10 | <10 | <10 | <10 | <10 | 80 | 1280 | 320 |
| DA₂PL + CPV | 8612 | <10 | <10 | <10 | <10 | <10 | 20 | 320 | 160 |
| | 8613 | <10 | <10 | <10 | <10 | <10 | 20 | 160 | 320 |
| Geometric mean | | <10 | <10 | <10 | <10 | <10 | 40 | 320 | 320 |
| 340 IPU | 8609 | <10 | <10 | <10 | <10 | <10 | 320 | 1280 | 320 |
| EML (50K AVU) | 8610 | <10 | <10 | <10 | <10 | <10 | 40 | 320 | 80 |
| DA₂PL + CPV | 8617 | <10 | <10 | <10 | <10 | <10 | <10 | <10 | <10 |
| Geometric mean | | <10 | <10 | <10 | <10 | <10 | 40 | 160 | 40 |
| 1340 IPU | 8607 | <10 | <10 | 320 | 1280 | 1280 | 640 | 1280 | 640 |
| EML (200K AVU) | 8615 | <10 | <10 | 320 | 640 | 1280 | 1280 | 2560 | 640 |
| DA₂PL + CPV | 8616 | <10 | <10 | 20 | 320 | 640 | 320 | 1280 | 160 |
| Geometric mean | | <10 | <10 | 160 | 640 | 1280 | 640 | 1280 | 320 |

*First dose of EML and/or vaccine was given 2/07/86.
**Second dose of EML and/or vaccine was given 3/07/86.

TABLE 7

Antibody Response to MLV Canine Parvovirus Vaccine - SN Titers.
The Effect of Equine Mixed Leukokine on Antibody Response to Modified Live
Virus Canine Parvovirus Combination Vaccine: Serum-virus Neutralization (SN) Titers

| Treatment Group | Dog No. | 2/07* | 2/14 | 2/21 | 2/28 | 3/07** | 3/14 | 3/21 | 3/28 |
|---|---|---|---|---|---|---|---|---|---|
| EML only | 8608 | <2 | <2 | <2 | <2 | <2 | <2 | <2 | <2 |
| (200K AVU) | 8614 | <2 | <2 | <2 | <2 | <2 | <2 | <2 | <2 |
| 1340 IPU | 8618 | <2 | <2 | <2 | <2 | <2 | <2 | <2 | <2 |
| Geometric mean | | <2 | <2 | <2 | <2 | <2 | <2 | <2 | <2 |
| Vaccine only | 8611 | <2 | <4 | <4 | <4 | <4 | 4 | 512 | 512 |
| DA₂PL + CPV | 8612 | <2 | <4 | <4 | <4 | <4 | <4 | 64 | 256 |
| | 8613 | <2 | <4 | <4 | <4 | <4 | <4 | 4 | 64 |
| Geometric mean | | <2 | <4 | <4 | <4 | <4 | <4 | 32 | 256 |
| EML 340 IPU | 8609 | <2 | <4 | <4 | <4 | <4 | 16 | 256 | 256 |
| (50K AVU) | 8610 | <2 | <4 | <4 | <4 | <4 | 32 | 64 | 32 |
| DA₂PL + CPV | 8617 | <2 | <4 | <4 | <4 | <4 | <4 | <4 | <4 |
| Geometric mean | | <2 | <4 | <4 | <4 | <4 | 8 | 32 | 16 |
| EML 1340 IPU | 8607 | <2 | <4 | <4 | 64 | 256 | 512 | 512 | 512 |
| (200K AVU | 8615 | <2 | <4 | <4 | 256 | 512 | 1024 | 2048 | 2048 |
| DA₂PL + CPV | 8616 | <2 | <4 | <4 | 4 | 254 | 256 | 512 | 1024 |
| Geometric mean | | <2 | <4 | <4 | 32 | 256 | 512 | 1024 | 1024 |

*First dose of EML and/or combination MLV vaccine was given 2/07/86.
**Second dose of EML and/or combination MLV vaccine was given 3/07/86.

As can be seen from the foregoing specific description, the EML of the present invention are very effective in increasing the serum antibody titer for equine influenza vaccine and canine parvovirus. Similar effects can be expected with other vaccines since the results should not depend upon a particular vaccine antigen.

We claim:

1. In a method for providing an immune response to a disease in a mammal with a viral or viral subunit or other viral antigen vaccine which produces a blood serum antibody response to the vaccine in the mammal the improvement which comprises:
   administering an equine leukokine with the vaccine to thereby provide an enhanced immune response in the mammal.

2. The method of claim 1 wherein the vaccine and leukokine are administered concurrently or in admixture to the mammal.

3. The method of claim 1 wherein prior to administration the leukokine has been induced by a virus in a medium containing leucocytes and then separated from the medium and leucocytes.

4. The method of claim 3 wherein the virus which induced the leukokine produces Newcastles disease in chickens.

5. The method of claim 1 wherein the vaccine is for canine parvovirus and is injected intramuscularly with the leukokine.

6. The method of claim 5 wherein an amount of at least 100 IPU of the leukokine are administered to the mammal with the vaccine.

7. The method of claim 1 wherein the leukokine and vaccine are administered separately and concurrently.

8. The method of claim 1 wherein the vaccine and leukokines are administered by injection.

9. The method of claim 1 wherein the administration is by injection, wherein the vaccine and leukokine are administered separately and concurrently and wherein the leukokine is induced in the leucocytes by a virus which produces Newcastles disease in chickens.

10. The method of claim 1 wherein the leukokine is an admixture of leukokines of different molecular size.

11. A vaccine composition for a mammal which comprises in admixture:
(a) a viral or viral subunit or other viral antigen vaccine which provides a blood serum antibody response to the vaccine in the mammal to provide an immune response to a viral disease; and
(b) an equine leukokine as an adjuvant to the vaccine, wherein the leukokine is present in an amount of at least about 100 IPU which enhances the blood serum antibody response to the vaccine in the mammal.

12. The vaccine composition of claim 11 wherein the leukokine prior to admixture has been induced by a virus in a medium containing leucocytes and then separated from the medium.

13. The vaccine composition of claim 12 wherein the virus which induced the leukokine produces Newcastles disease in chickens.

14. The vaccine composition of claim 11 wherein the leukokines are a mixture of leukokines of different molecular size.

15. A parvovirus vaccine composition for a canine which comprises in admixture:
(a) a parvovirus vaccine which produces a blood serum antibody response to the vaccine in the canine to provide parvovirus immunity; and
(b) an equine leukokine as an adjuvant to the vaccine, wherein the leukokine is present in an amount of at least about 100 IPU which enhances the blood serum antibody response to the vaccine in the canine by providing immunity at an earlier age.

16. The vaccine composition of claim 15 wherein between about 100 and 5000 IPU of the leukokines in the vaccine are administered.

17. The vaccine composition of claim 16 wherein the vaccine is administered in a dosage between about 0.1 and 5 ml.

* * * * *

UNITED STATES PATENT AND TRADEMARK OFFICE
CERTIFICATE OF CORRECTION

PATENT NO. : 4,689,224

DATED : August 25, 1987

INVENTOR(S) : Robert W. Bull, Robert M. Soltysiak, Paul D. Minnick

It is certified that error appears in the above-identified patent and that said Letters Patent are hereby corrected as shown below:

Column 2, line 45 after "result", --of-- should be inserted.

Column 3, line 23 "aobut" should be --about--.

Column 4, line 1 after "absorption", --vaccines-- should be inserted.

Column 4, line 58 "or" should be --of--.

Column 7, line 27 "0.02" should be --0.02%--.

Column 7, line 56 "Viral" should be --Virus--.

Column 8, line 5 "stat" should be --state--.

Column 8, line 10 "commercial" should be --commercially--.

Column 8, line 15 "resonses" should be --responses--.

Column 8, line 37 before "30", --for-- should be inserted.

Column 8, line 47 at "2." should begin a new paragraph.

Column 8, line 48 afater "PBS", --was-- should be inserted--.

UNITED STATES PATENT AND TRADEMARK OFFICE
CERTIFICATE OF CORRECTION

PATENT NO. : 4,689,224

DATED : August 25, 1987

INVENTOR(S) : Robert W. Bull, Robert M. Soltysiak, Paul D. Minnick

It is certified that error appears in the above-identified patent and that said Letters Patent are hereby corrected as shown below:

Column 9, lines 12 and 13 "titled" should be --tilted--.

Column 9, line 47 "-EML" should be --no EML--.

Column 9, line 66 "regiment" should be --regimen--.

Column 10, line 20 "equie" should be --equi--.

Column 10, line 43 "Equicine TM" should be --Equicine II™--.

Column 12, line 11 "great" should be --greatest--.

Column 14, line 4 "filter" should be --first--.

Column 14, line 4 "shows" should be --shown--.

Column 14, line 27 "1340)IPU)" shoudl be --(1340 IPU)--.

Signed and Sealed this

Twenty-third Day of February, 1988

*Attest:*

DONALD J. QUIGG

*Attesting Officer*      *Commissioner of Patents and Trademarks*